(12) United States Patent
Wagner et al.

(10) Patent No.: US 8,968,411 B2
(45) Date of Patent: Mar. 3, 2015

(54) MODULAR ELBOW PROSTHESIS

(75) Inventors: Terry W. Wagner, Michawaka, IN (US); Brian Kincaid, Warsaw, IN (US); Kent Walz, Fort Wayne, IN (US); Shawn E. McGinley, Fort Wayne, IN (US); Stephen H. Hoag, Warsaw, IN (US)

(73) Assignee: Zimmer, Inc., Warsaw, IN (US)

(*) Notice: Subject to any disclaimer, the term of this patent is extended or adjusted under 35 U.S.C. 154(b) by 188 days.

(21) Appl. No.: 12/856,112

(22) Filed: Aug. 13, 2010

(65) Prior Publication Data

US 2011/0153024 A1    Jun. 23, 2011

Related U.S. Application Data

(60) Provisional application No. 61/287,526, filed on Dec. 17, 2009.

(51) Int. Cl.
*A61F 2/38* (2006.01)
*A61F 2/30* (2006.01)

(52) U.S. Cl.
CPC ..... *A61F 2/3804* (2013.01); *A61F 2002/30383* (2013.01); *A61F 2002/30387* (2013.01); *A61F 2002/30505* (2013.01); *A61F 2002/30507* (2013.01); *A61F 2002/30565* (2013.01); *A61F 2002/3813* (2013.01)
USPC ..................................................... 623/20.11

(58) Field of Classification Search
None
See application file for complete search history.

(56) References Cited

U.S. PATENT DOCUMENTS

| | | |
|---|---|---|
| 750,678 A | 1/1904 | Morton |
| 1,110,528 A | 9/1914 | Borresen |
| 1,517,162 A | 11/1924 | King |
| 1,677,365 A | 7/1928 | Peck |
| 2,462,536 A | 2/1949 | Muter |
| 2,737,917 A | 3/1956 | Steele |
| 2,837,951 A | 6/1958 | Phelps |
| 3,157,075 A | 11/1964 | Filia |
| 3,187,751 A | 6/1965 | Coren |
| 3,563,124 A | 2/1971 | Gargrave |
| 3,641,652 A | 2/1972 | Arnold et al. |
| 3,708,805 A | 1/1973 | Scales et al. |
| 3,816,854 A | 6/1974 | Schlein |
| 3,826,160 A | 7/1974 | Allen et al. |

(Continued)

FOREIGN PATENT DOCUMENTS

| | | |
|---|---|---|
| FR | 2579454 A1 | 10/1986 |
| FR | 2660857 B1 | 12/1997 |

(Continued)

OTHER PUBLICATIONS

Brochure "The Ball Lock System—Dayton True Position Retainers", 2002 Dayton Progress Corporation.

(Continued)

*Primary Examiner* — Thomas J Sweet
*Assistant Examiner* — Rebecca Preston
(74) *Attorney, Agent, or Firm* — Schwegman Lundberg & Woessner, P.A.

(57) ABSTRACT

A modular elbow prosthesis including an ulnar component and a humeral component. The ulnar component includes an ulnar head and an ulnar stem. The humeral component includes a humeral head and a humeral stem. The humeral component also includes a locking system for securing the humeral head onto the humeral stem.

22 Claims, 13 Drawing Sheets

(56) References Cited

U.S. PATENT DOCUMENTS

| | | | |
|---|---|---|---|
| 4,038,704 A | 8/1977 | Ring | |
| 4,227,299 A | 10/1980 | Kuehling | |
| 4,280,231 A | 7/1981 | Swanson | |
| 4,365,411 A | 12/1982 | Muldoon | |
| 4,383,337 A | 5/1983 | Volz et al. | |
| 4,420,879 A | 12/1983 | Harringer | |
| 4,822,364 A | 4/1989 | Inglis et al. | |
| 4,982,631 A | 1/1991 | Lowther | |
| 5,020,399 A | 6/1991 | Annis et al. | |
| 5,061,271 A | 10/1991 | Van Zile | |
| 5,197,368 A | 3/1993 | Meyer et al. | |
| 5,314,479 A | 5/1994 | Rockwood, Jr. et al. | |
| 5,376,121 A | 12/1994 | Huene et al. | |
| 5,702,457 A | 12/1997 | Walch et al. | |
| 5,702,486 A | 12/1997 | Craig et al. | |
| 5,723,015 A | 3/1998 | Risung et al. | |
| 5,961,555 A | 10/1999 | Huebner | |
| 6,027,534 A | 2/2000 | Wack et al. | |
| 6,102,953 A | 8/2000 | Huebner | |
| 6,129,764 A | 10/2000 | Servidio | |
| 6,168,630 B1 | 1/2001 | Keller et al. | |
| 6,197,063 B1 | 3/2001 | Dews | |
| 6,290,725 B1 | 9/2001 | Weiss et al. | |
| 6,314,843 B1 | 11/2001 | Wiebe et al. | |
| 6,379,387 B1 | 4/2002 | Tornier | |
| 6,673,114 B2 | 1/2004 | Hartdegen et al. | |
| 6,699,290 B1 | 3/2004 | Wack et al. | |
| 6,716,248 B2 | 4/2004 | Huene | |
| 6,739,068 B1 | 5/2004 | Rinner | |
| 6,767,368 B2 | 7/2004 | Tornier | |
| 6,890,357 B2 | 5/2005 | Tornier | |
| 6,923,832 B1 | 8/2005 | Sharkey et al. | |
| 6,964,088 B2 | 11/2005 | Crevoisier | |
| 6,969,407 B2 | 11/2005 | Klotz et al. | |
| 7,097,663 B1 | 8/2006 | Nicol et al. | |
| 7,247,170 B2 | 7/2007 | Graham et al. | |
| 7,338,528 B2 | 3/2008 | Stone et al. | |
| 7,604,666 B2 | 10/2009 | Berelsman et al. | |
| 7,625,406 B2 | 12/2009 | Berelsman et al. | |
| 7,722,625 B2 | 5/2010 | Sanders et al. | |
| 7,846,376 B2 | 12/2010 | Abt et al. | |
| 7,850,737 B2 | 12/2010 | Morrey | |
| 8,328,873 B2 | 12/2012 | Metzger et al. | |
| 2001/0021876 A1* | 9/2001 | Terrill-Grisoni et al. | 623/20.11 |
| 2002/0156534 A1 | 10/2002 | Grusin et al. | |
| 2002/0165614 A1* | 11/2002 | Tornier | 623/20.12 |
| 2003/0144739 A1 | 7/2003 | Huene | |
| 2003/0208277 A1 | 11/2003 | Weiss | |
| 2004/0186581 A1* | 9/2004 | Huene | 623/20.12 |
| 2004/0193268 A1* | 9/2004 | Hazebrouck | 623/16.11 |
| 2004/0193276 A1 | 9/2004 | Maroney et al. | |
| 2004/0243243 A1* | 12/2004 | Tornier | 623/20.12 |
| 2005/0043806 A1 | 2/2005 | Cook et al. | |
| 2005/0075735 A1* | 4/2005 | Berelsman et al. | 623/20.11 |
| 2006/0100712 A1 | 5/2006 | Ball | |
| 2006/0100713 A1 | 5/2006 | Ball | |
| 2006/0111788 A1 | 5/2006 | Ball | |
| 2006/0111789 A1 | 5/2006 | Ball | |
| 2006/0173546 A1 | 8/2006 | Berelsman et al. | |
| 2006/0224243 A1 | 10/2006 | Pare et al. | |
| 2006/0247786 A1* | 11/2006 | Ball | 623/20.13 |
| 2007/0129808 A1* | 6/2007 | Justin et al. | 623/20.15 |
| 2007/0282450 A1 | 12/2007 | Habermeyer et al. | |
| 2007/0299527 A1 | 12/2007 | McCleary et al. | |
| 2008/0015706 A1 | 1/2008 | Berelsman et al. | |
| 2008/0033566 A1 | 2/2008 | Berelsman et al. | |
| 2008/0114461 A1 | 5/2008 | Collazo | |
| 2008/0306601 A1 | 12/2008 | Dreyfuss | |
| 2009/0024221 A1 | 1/2009 | Ball | |
| 2009/0105839 A1 | 4/2009 | Ikegami et al. | |
| 2010/0051141 A1 | 3/2010 | Bhambri | |
| 2010/0087928 A1 | 4/2010 | Graham et al. | |
| 2010/0160985 A1 | 6/2010 | Pannu | |
| 2010/0179661 A1 | 7/2010 | Berelsman et al. | |
| 2010/0222887 A1* | 9/2010 | Katrana et al. | 623/20.11 |
| 2011/0125274 A1* | 5/2011 | Bartel et al. | 623/20.11 |
| 2011/0172781 A1 | 7/2011 | Katrana et al. | |
| 2012/0000326 A1 | 1/2012 | Sheriff | |
| 2012/0095473 A1 | 4/2012 | Soliman et al. | |
| 2013/0340236 A1 | 12/2013 | Wagner et al. | |
| 2013/0345818 A1 | 12/2013 | Wagner et al. | |

FOREIGN PATENT DOCUMENTS

| | | |
|---|---|---|
| WO | WO97/25943 A1 | 7/1997 |
| WO | WO2006/129495 A1 | 12/2006 |
| WO | WO2008/002545 A2 | 1/2008 |
| WO | WO-2010098791 A2 | 9/2010 |
| WO | WO-2011060430 A2 | 5/2011 |
| WO | WO-2013192408 A1 | 12/2013 |

OTHER PUBLICATIONS

Surgical Technique "Zimmer Coonrad/Morrey Total Elbow, Interchangeability, Anterior Flange, Clinical History," 97-8106-102-00 Rev. 2, Zimmer, Inc. 2002, 2005, 2009.

Surgical Technique for Revision "Zimmer Coonrad/Morrey Total Elbow Arthroplasty—Impaction Grafting Procedure," Zimmer, Inc.

Brochure "Zimmer Coonrad/Morrey Total Elbow, Interchangeability, Anterior Flange, Clinical Success," 97-8106-301-00 Zimmer, Inc. 2000, 2006, 2007.

"U.S. Appl. No. 13/800,567, Restriction Requirement mailed Sep. 10, 2013", 7 pgs.

"U.S. Appl. No. 13/800,650, Preliminary Amendment filed Aug. 8, 2013", 7 pgs.

"International Application Serial No. PCT/US2013/046792, International Search Report mailed Aug. 23, 2013", 6 pgs.

"International Application Serial No. PCT/US2013/046792, Written Opinion mailed Aug. 23, 2013", 7 pgs.

"U.S. Appl. No. 13/800,567, Non Final Office Action mailed Jan. 29, 2014", 14 pgs.

"U.S. Appl. No. 13/800,567, Response filed May 29, 2014 to Non Final Office Action mailed Jan. 29, 2014", 19 pgs.

\* cited by examiner

MODULAR ELBOW PROSTHESIS

CROSS REFERENCE TO RELATED APPLICATION

This application claims priority from U.S. Provisional Patent Application Ser. No. 61/287,526, entitled "MODULAR ELBOW PROSTHESIS," filed Dec. 17, 2009, the disclosure of which is hereby expressly incorporated by reference herein in its entirety.

BACKGROUND

1. Field of the Invention

The present invention relates to an orthopaedic prosthesis. More particularly, the present invention relates to a modular elbow prosthesis.

2. Description of the Related Art

A joint arthroplasty procedure may be performed to repair or replace damaged bone of a patient's joint, such as bone that is damaged due to a traumatic injury or a degenerative illness. For example, during a total elbow arthroplasty procedure, the surgeon implants a prosthetic humeral component into the distal end of a patient's humerus and a prosthetic ulnar component into the proximal end of the patient's ulna. The prosthetic humeral component and the prosthetic ulnar component are generally joined by a hinge that enables pivoting movement between the prosthetic humeral component and the prosthetic ulnar component to recreate the natural, anatomical articulation of the elbow joint.

SUMMARY

The present invention provides a modular elbow prosthesis including an ulnar component and a humeral component. The ulnar component includes an ulnar head and an ulnar stem. The humeral component includes a humeral head and a humeral stem. The humeral component also includes a locking system for securing the humeral head onto the humeral stem.

According to an embodiment of the present invention, an elbow prosthesis having an anterior side and a posterior side is provided. The elbow prosthesis includes a stem, a head, and a lock that releasably secures the head onto the stem. The stem has a longitudinal axis, the stem including a first mating surface that extends from the posterior side of the elbow prosthesis toward the anterior side of the elbow prosthesis at an angle relative to the longitudinal axis. The head is selectively coupled to the stem, the head including a second mating surface that abuts the first mating surface of the stem.

According to another embodiment of the present invention, an elbow prosthesis is provided including a stem having a longitudinal axis, a head, a sliding connection, and a locking feature for releasably securing the head onto the stem. The sliding connection includes a rail that extends from one of the stem and the head and a slot formed in the other of the stem and the head, the rail being sized to slide within the slot along a sliding axis to couple the head to the stem, the sliding axis and the longitudinal axis defining an angle therebetween.

According to yet another embodiment of the present invention, a method is provided for repairing a bone of a patient's elbow joint. The method includes the steps of providing a prosthesis including a head and a stem, the stem having an anterior side, a posterior side, and a longitudinal axis; sliding the head from the posterior side toward the anterior side of the stem along a sliding axis that is angled relative to the longitudinal axis to couple the head to the stem; locking the head onto the stem; and implanting the stem into the bone.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein.

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION

Figure 1:
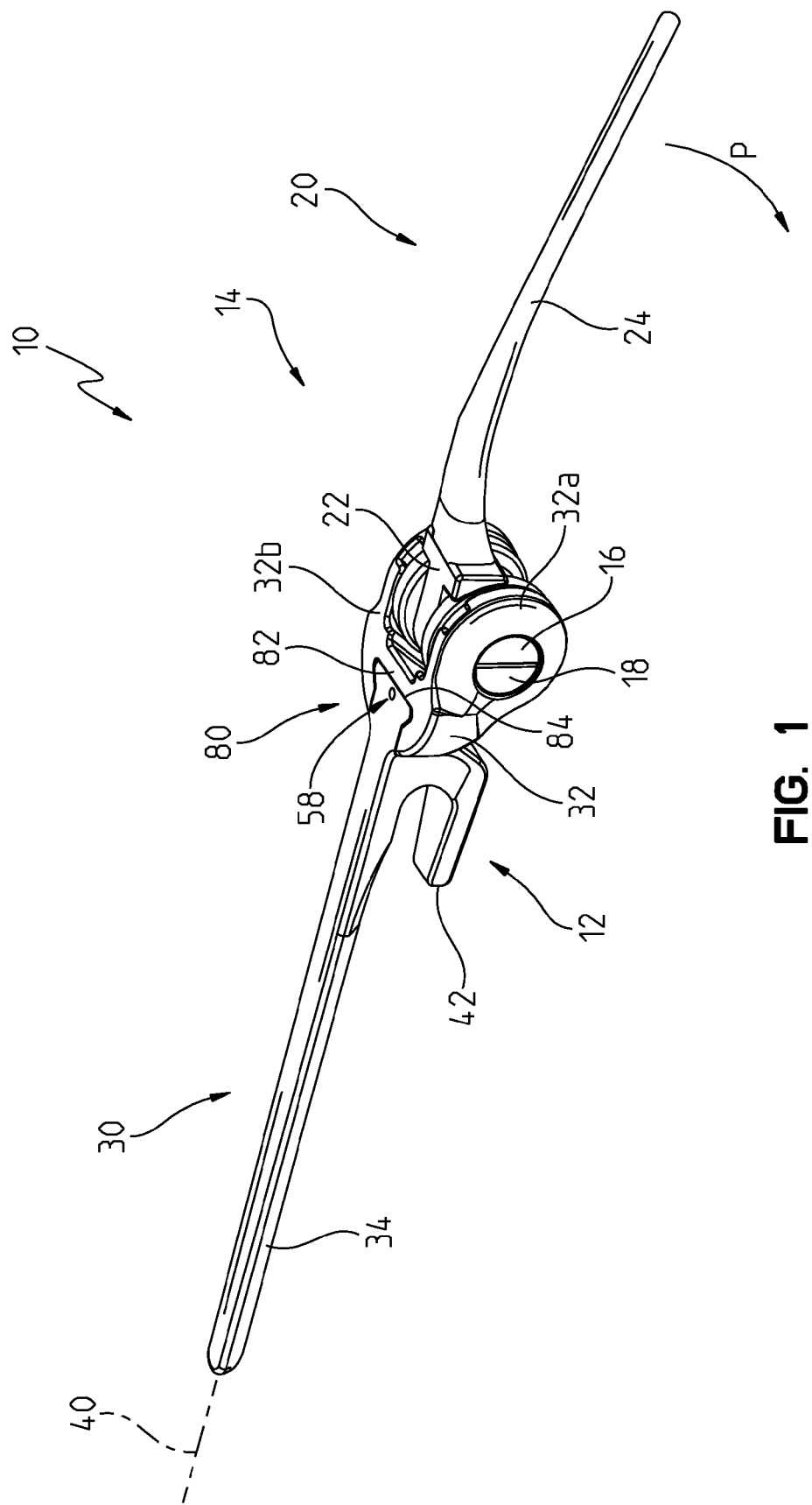
FIG. 1 is a perspective view of an exemplary elbow prosthesis of the present invention, the elbow prosthesis including an ulnar component and a humeral component.

FIG. 1 provides an exemplary elbow prosthesis 10 configured for implantation into a patient's elbow joint. Elbow prosthesis 10 has anterior side 12 and posterior side 14. When implanted, anterior side 12 of elbow prosthesis 10 faces anteriorly, and posterior side 14 of elbow prosthesis 10 faces posteriorly.

Elbow prosthesis 10 includes ulnar component 20 having ulnar head 22 and ulnar stem 24 and humeral component 30 having humeral yoke head or yoke 32 and humeral stem 34. During an elbow arthroplasty procedure, a surgeon implants ulnar component 20 into the proximal end of the patient's ulna (not shown) and humeral component 30 into the distal end of a patient's humerus (not shown). More particularly, the surgeon implants ulnar stem 24 into the intramedullary canal of the patient's ulna (not shown) and humeral stem 34 into the intramedullary canal of the patient's humerus (not shown).

With ulnar stem 24 and humeral stem 34 implanted into the patient's ulna and humerus, respectively, ulnar head 22 and humeral yoke 32 remain exposed to enable articulation. As shown in FIG. 1, humeral yoke 32 is a fork-shaped component having two spaced apart branches 32a, 32b, and ulnar head 22 is sized and shaped for receipt between those branches 32a, 32b. Ulnar head 22 and humeral yoke 32 are joined together by pivot pin 16 that extends transversely to ulnar stem 24 and humeral stem 34 to enable pivoting movement of ulnar component 20 relative to humeral component 30 in the direction of arrow P. Pivot pin 16 extends through bore 36a (FIG. 2) in first branch 32a of humeral yoke 32, through a bore (not shown) in ulnar head 22, and through bore 36b (FIG. 2) in second branch 32b of humeral yoke 32. Pivot pin 16 may have enlarged ends 18, as shown in FIG. 1, to prevent axial movement of pivot pin 16 between ulnar head 22 and humeral yoke 32.

Humeral component 30 of elbow prosthesis 10 is shown in more detail in FIGS. 2-9. Humeral component 30 includes longitudinal axis 40. Humeral component 30 also includes flange 42 that extends outwardly from anterior side 12 of humeral stem 34, bends proximally, and extends proximally in a direction parallel to longitudinal axis 40. In operation, the surgeon may clamp a bone graft (not shown) and the bone of the patient's humerus (not shown) between humeral stem 34 and flange 42. The clamping force exerted on the bone graft and the bone of the humerus prevents humeral stem 34 from rotating within the bone and also encourages ingrowth between the bone graft and the bone of the humerus.

Figure 2:
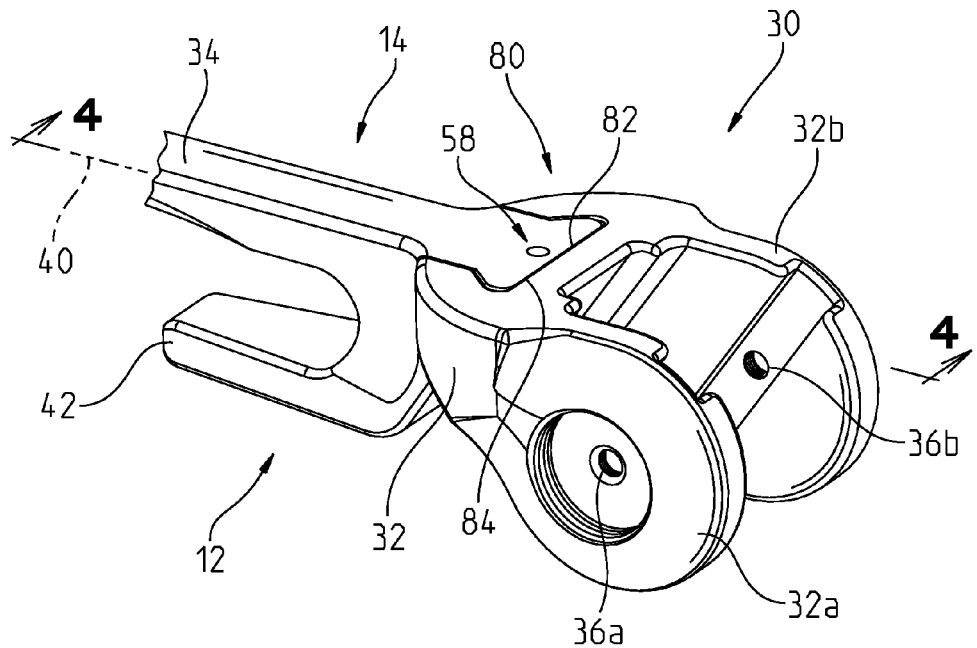
FIG. 2 is a perspective view of a portion of the humeral component of FIG. 1.

Referring to FIG. 2, humeral component 30 is a modular construct with humeral yoke 32 being selectively coupled to humeral stem 34. This modularity is beneficial both before and after the initial surgical procedure. Before the initial surgical procedure, the surgeon may select a desired humeral yoke 32 from a set to accommodate varying patient anatomies. The set may include prosthetic humeral heads of different sizes and types to enable a patient-specific surgical solution. For example, although humeral yoke 32 of FIG. 1 is designed to articulate with a prosthetic ulnar head 22 following a total elbow arthroplasty procedure, the set may include a prosthetic humeral head that is designed to articulate with the patient's natural ulna following a hemi-arthroplasty procedure. After the initial surgical procedure, the surgeon may remove and replace humeral yoke 32 without having to remove humeral stem 34 from the intramedullary canal of the patient's humerus (not shown). For example, should a total arthroplasty procedure become necessary following an initial hemi-arthroplasty procedure, the surgeon may remove and replace a hemi-head with a total head while leaving humeral stem 34 in place. Also, should the articulating region of humeral yoke 32 become worn or otherwise damaged, the surgeon may remove and replace the worn humeral yoke 32 with a new humeral yoke 32 while leaving humeral stem 34 in place. Additionally, the modularity of humeral component 30 allows full seating of the humeral stem 34 in the intramedullary canal of the humerus prior to attaching humeral yoke 32 and/or establishing the critical linkage of elbow prosthesis 10, i.e. the connection between humeral component 30 and ulnar component 20.

Figure 4:
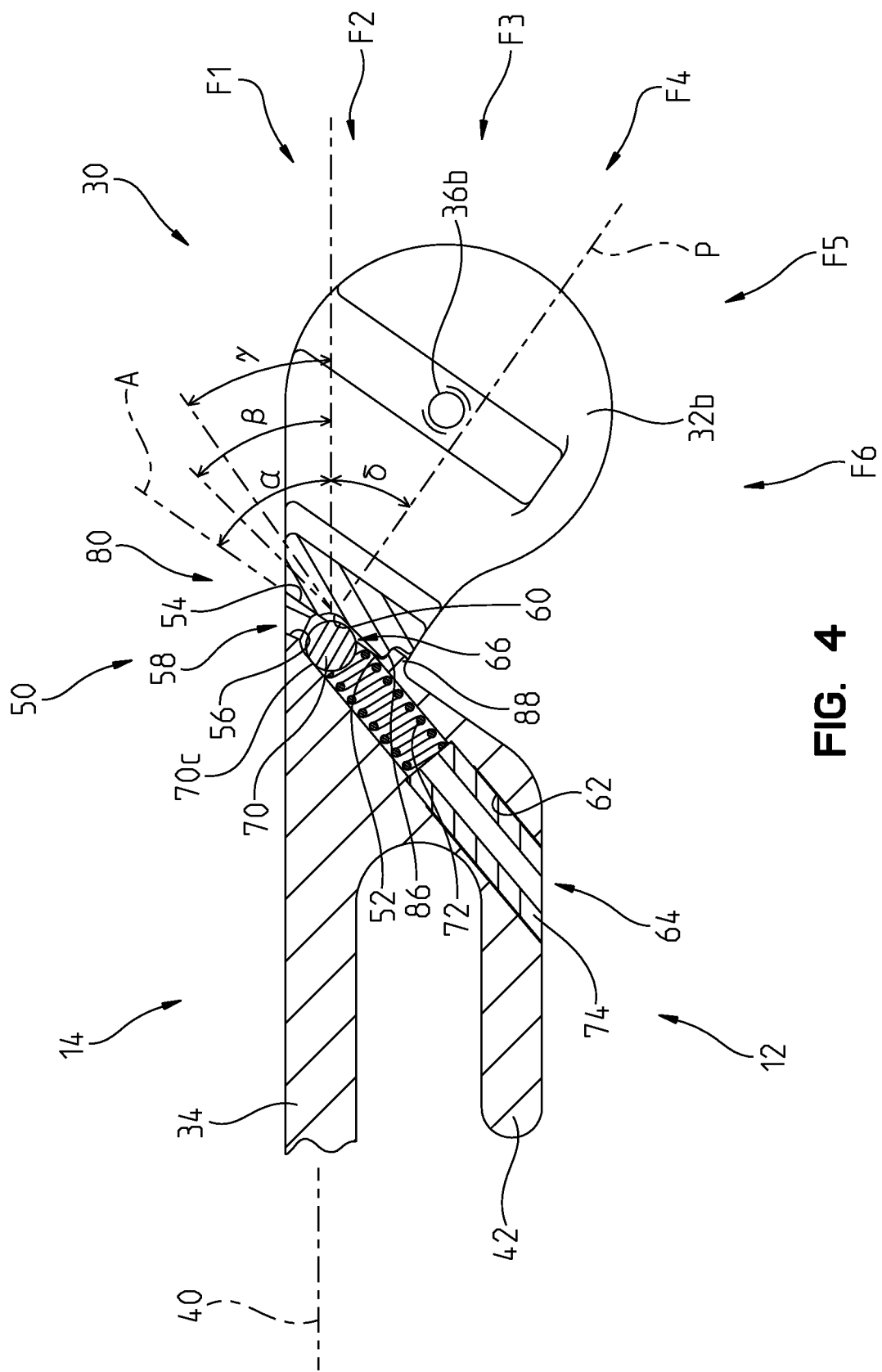
FIG. 4 is a cross-sectional view of the humeral component of FIG. 2, taken along line 4-4 of FIG. 2.
Figure 5:
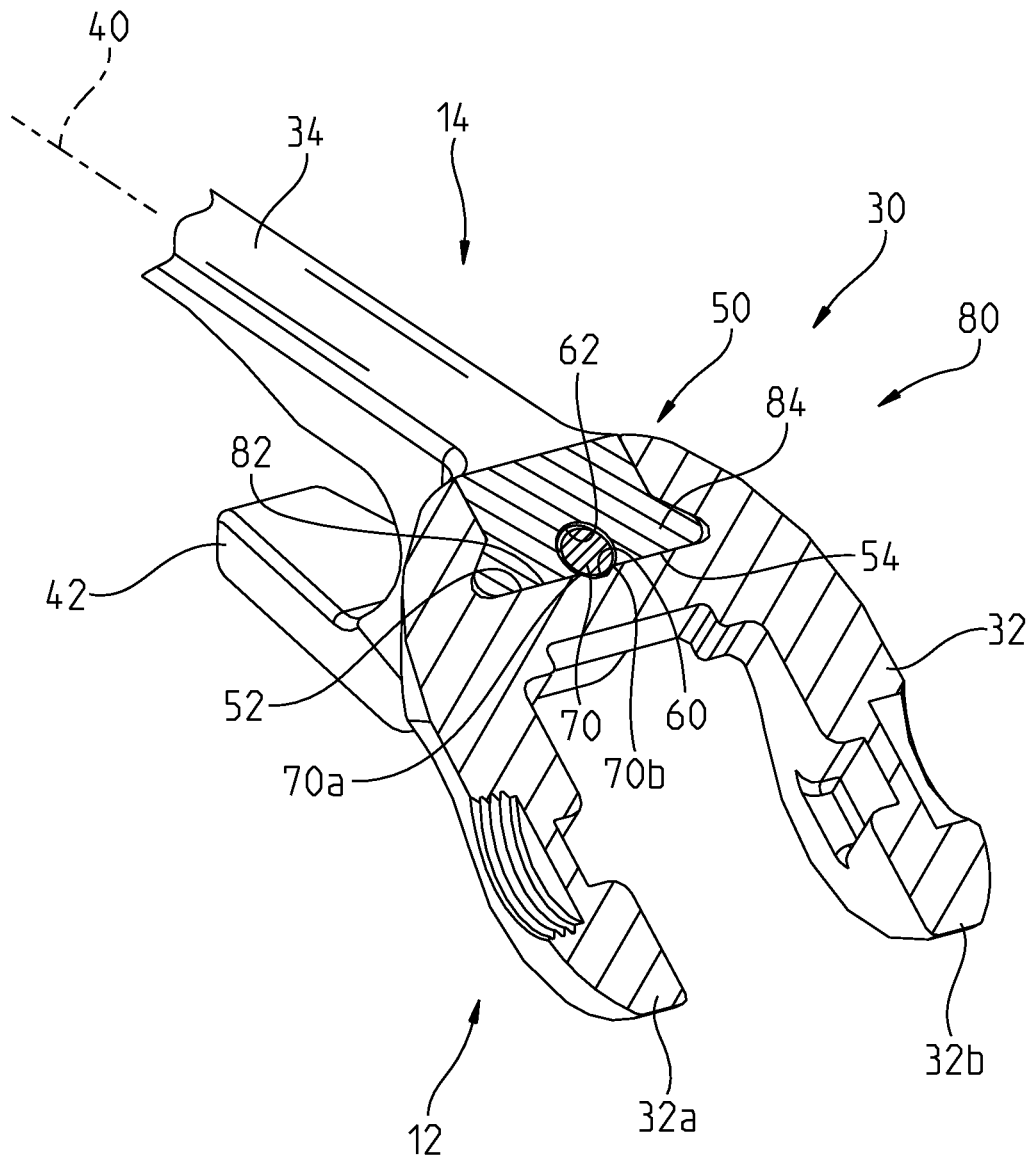
FIG. 5 is a cross-sectional view of the humeral component of FIG. 3, taken along line 5-5 of FIG. 3.
Figure 6:
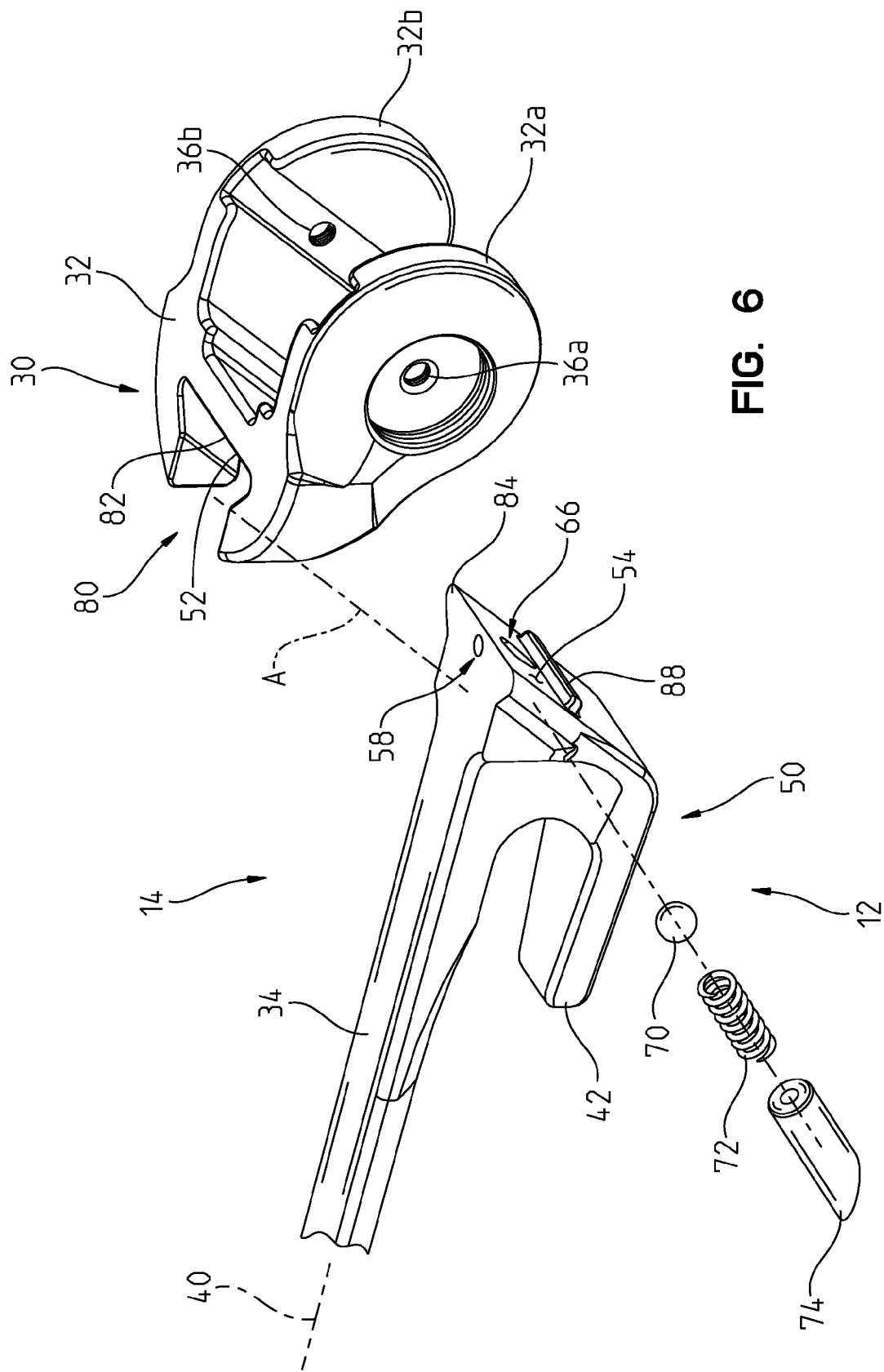
FIG. 6 is a posterior exploded perspective view of the humeral component of FIG. 2.

As shown in FIGS. 4 and 5, humeral yoke 32 includes mating surface 52 and humeral stem 34 includes mating surface 54. From posterior side 14 to anterior side 12, mating surfaces 52, 54, extend proximally and away from ulnar component 20 (FIG. 1). As shown in FIG. 4, mating surfaces 52, 54, are angled at angle α relative to longitudinal axis 40 of humeral component 30. Angle α may equal approximately 45°, 50°, 55°, 60°, or 65°, for example.

Referring next to FIGS. 3-7, humeral component 30 includes locking system 50 for releasably securing the desired humeral yoke 32 onto humeral stem 34. Locking system 50 enables mating surface 52 of humeral yoke 32 to lock against mating surface 54 of humeral stem 34. According to an exemplary embodiment of the present invention, locking system 50 is a ball lock retention system.

Figure 8:
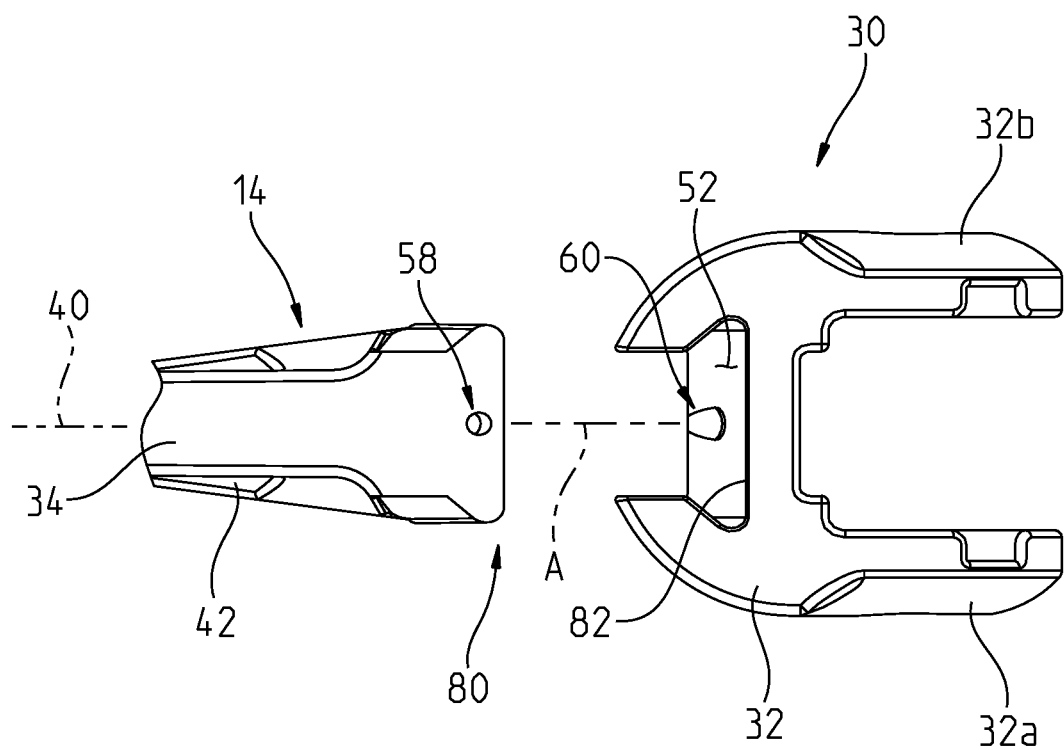
FIG. 8 is a posterior plan view of the humeral component of FIG. 2.
Figure 9:
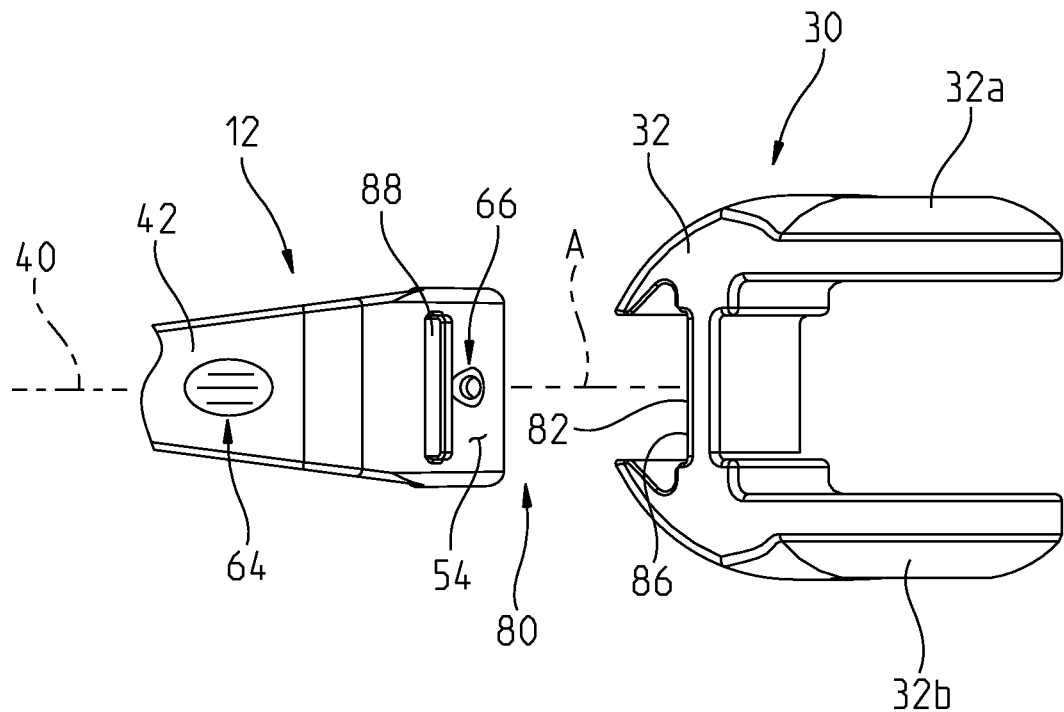
FIG. 9 is an anterior plan view of the humeral component of FIG. 2.

As shown in FIGS. 4 and 8, mating surface 52 of humeral yoke 32 defines recess 60. According to an exemplary embodiment of the present invention, recess 60 is a teardrop shaped cavity. As shown in FIG. 4, recess 60 defines angle β relative to longitudinal axis 40 of humeral component 30. Angle β may be approximately 10° to 13° less than angle α, for example.

As shown in FIG. 4, humeral stem 34 includes channel 62 that extends entirely through humeral stem 34 from a first, axial opening 64 in anterior side 12 of humeral stem 34 to a second, radial opening 66 in mating surface 54 of humeral stem 34. Channel 62 may extend at least partially through flange 42 of humeral stem 34, as shown in FIG. 4, such that axial opening 64 is formed in flange 42. Channel 62 defines angle γ relative to longitudinal axis 40 of humeral component 30. Angle γ may be approximately 15° less than angle α, for example.

Locking system 50 includes locking ball 70, compression spring 72, and plug 74, that are received within channel 62 of humeral stem 34. Spring 72 is axially fixed within channel 62 such that spring 72 imparts an axial force on locking ball 70. In one embodiment, spring 72 may be a self-locking component that expands outwardly against the walls of channel 62 to maintain a fixed axial position within channel 62. In another embodiment, spring 72 may be held axially in place within channel 62 by plug 74. With spring 72 fixed axially in place, spring 72 forces locking ball 70 toward radial opening 66 of channel 62. As shown in FIGS. 4 and 5, a portion of locking ball 70 protrudes from radial opening 66 of channel 62, beyond mating surface 54 of humeral stem 34 and toward mating surface 52 of humeral yoke 32. The diameter of radial opening 66 is smaller than the diameter of locking ball 70, so locking ball 70 does not exit channel 62 through radial opening 66 under the force of spring 72.

To connect or disconnect mating surfaces 52, 54, the surgeon must remove locking ball 70 from radial opening 66 by forcing locking ball 70 into channel 62. Unlike a typical detent mechanism, forces on locking ball 70 via radial opening 66 act transversely to spring 72, not parallel to spring 72. Thus, forces on locking ball 70 via radial opening 66 do not force locking ball 70 into channel 62. To enable removal of locking ball 70 from radial opening 66, humeral stem 34 includes release slot 56. As shown in FIG. 4, release slot 56 extends from channel 62 to release opening 58 in posterior side 14 of humeral stem 34. In operation, the surgeon inserts a tool (not shown), such as an elongate bar or a threaded tool, into release slot 56 of humeral stem 34. Pushing the tool through release slot 56 and against locking ball 70 compresses spring 72 and releases locking ball 70 from radial opening 66. Then, the surgeon is able to connect or disconnect mating surfaces 52, 54.

When the tool (not shown) is removed from release slot 56, locking ball 70 again projects from radial opening 66 under the force of spring 72. With mating surface 52 of humeral yoke 32 positioned against mating surface 54 of humeral stem 34, as shown in FIG. 4, locking ball 70 projects into recess 60 of humeral yoke 32 to lock humeral yoke 32 onto humeral stem 34. In this locked position, locking ball 70 does not ride to the end of channel 62 near posterior side 14 or to the end of recess 60 near posterior side 14, but assumes an intermediate position spaced away from posterior side 14, as shown in FIG. 4. Also, in this locked position, locking ball 70 contacts both humeral yoke 32 and humeral stem 34. Specifically, two spaced apart points 70a, 70b, of locking ball 70 contact recess 60 of humeral yoke 32, as shown in FIG. 5, and another point 70c of locking ball 70 contacts the wall of channel 62 in humeral stem 34, as shown in FIG. 4. As discussed above, forces on locking ball 70 via radial opening 66 do not force locking ball 70 out of this locked position and into channel 62. Thus, forces on locking ball 70 from humeral yoke 32 do not force locking ball 70 out of this locked position and into channel 62, ensuring a reliable connection between humeral yoke 32 and humeral stem 34.

An exemplary ball lock retention system is the Ball Lock System generally available from Dayton Progress Corporation of Dayton, Ohio. Other exemplary ball lock retention systems are described in U.S. Pat. Nos. 3,563,124 and 5,197,368, the disclosures of which are expressly incorporated by reference herein.

According to an exemplary embodiment of the present invention, humeral yoke 32 is connected to humeral stem 34 via a sliding connection, such as dovetail connection 80. Humeral yoke 32 and humeral stem 34 are configured to slide along axis A of dovetail connection 80, which is parallel to mating surfaces 52, 54. As shown in FIG. 5, humeral yoke 32 includes a trapezoidal slot 82 and humeral stem 34 includes a corresponding trapezoidal rail 84 that is sized for receipt within slot 82. Mating surface 52 of humeral yoke 32 is located on the bottom of slot 82, and mating surface 54 of humeral stem 34 is located on the top of rail 84. Advantageously, locking system 50 may span from flange 42 to rail 84 of humeral stem 34, providing adequate space for channel 62, locking ball 70, spring 72, and plug 74.

Figure 7:
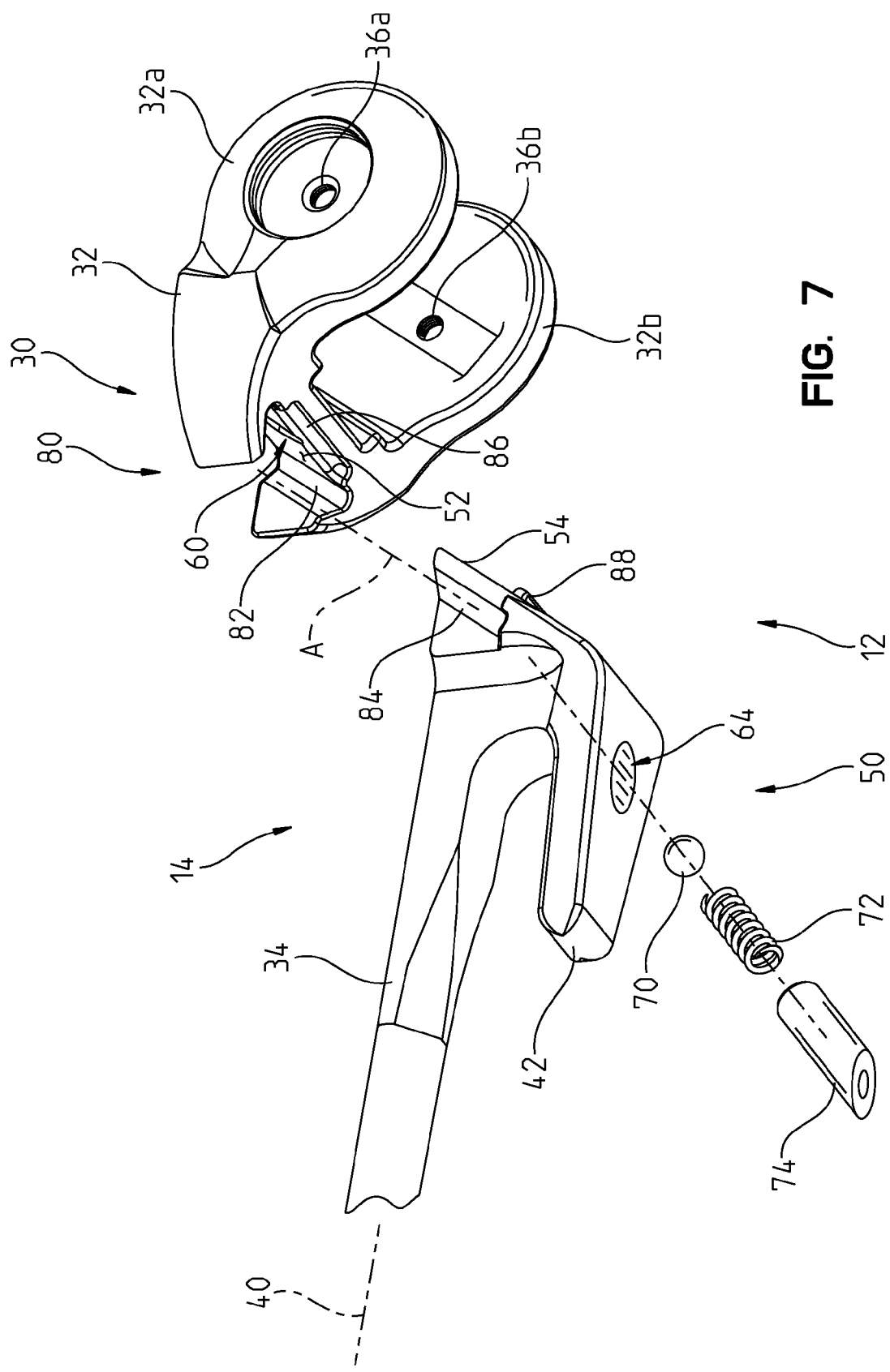
FIG. 7 is an anterior exploded perspective view of the humeral component of FIG. 2.

In operation, the surgeon first presses locking ball 70 into channel 62. Then, the surgeon slides humeral yoke 32 onto posterior side 14 of humeral stem 34 in an anterior direction along axis A. The ability to connect and disconnect humeral yoke 32 from posterior side 14 of humeral stem 34 accommodates a posterior surgical approach. As shown in FIG. 7, humeral yoke 32 includes groove 86 and humeral stem 34 includes stop or tab 88 that projects from humeral stem 34 and into groove 86 of humeral yoke 32 to support humeral yoke 32 and to prevent excessive anterior movement of humeral yoke 32. With humeral yoke 32 in place, the surgeon releases locking ball 70 to lock humeral yoke 32 onto humeral stem 34.

To stabilize the connection between humeral yoke 32 and humeral stem 34 and to reduce micro-motion, dovetail connection 80 may be a tapered connection. For example, slot 82 and rail 84 may taper inwardly toward axis A from posterior side 14 to anterior side 12 of humeral component 30.

Figure 3:
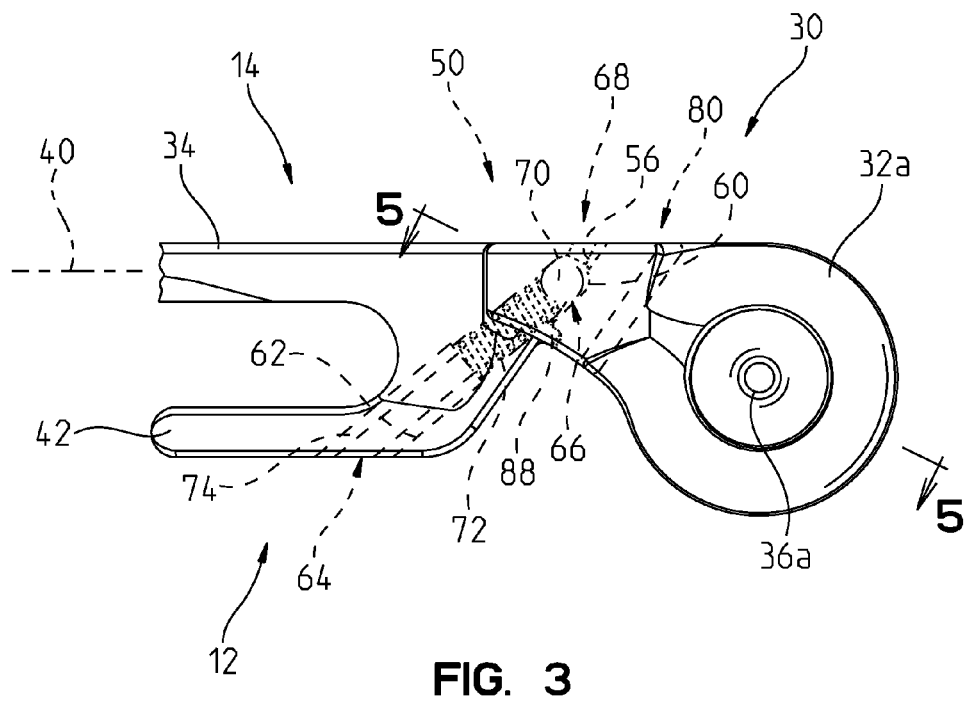
FIG. 3 is an elevational view of the humeral component of FIG. 2.

Referring next to FIGS. 3 and 4, when humeral component 30 is implanted in the patient's body, the patient's natural ulna (not shown) or ulnar component 20 applies a joint reaction force F to humeral component 30. As ulnar component 20 pivots relative to humeral component 30, the angle between force F and longitudinal axis 40 of humeral component 30 ("Average Joint Reaction Force Angle") changes. The relationship between the ulnar flexion angle and the Average Joint Reaction Force Angle is set forth in Table 1 below. An ulnar flexion angle of 0° indicates that the patient's arm is fully extended.

TABLE 1

| Ulnar Flexion Angle | Average Joint Reaction Force | Average Joint Reaction Force Angle |
|---|---|---|
| 0° | $F_1$ | −9° |
| 30° | $F_2$ | 5° |
| 60° | $F_3$ | 21° |
| 90° | $F_4$ | 33° |
| 120° | $F_5$ | 58° |
| 145° | $F_6$ | 77° |

As shown in FIG. 4, normal plane P extends perpendicular to axis A of dovetail connection 80. If angle α between mating surfaces 52, 54, and longitudinal axis 40 equals approximately 55°, for example, angle δ between normal plane P and longitudinal axis 40 equals approximately 35°.

During initial flexion of ulnar component 20, the angle between force F and longitudinal axis 40 is less than angle δ. For example, between 0-90° of ulnar flexion, the Average Joint Reaction Force Angle is less than angle δ of 35° (See Table 1). Within that range, force F is a beneficial, compressive force that acts on humeral yoke 32 to force humeral yoke 32 into engagement with humeral stem 34. For example, force F will force humeral yoke 32 toward tab 88 of humeral stem 34. Advantageously, humans' elbow joints are most often held within the initial flexion range, specifically 30-90° of ulnar flexion, so the compressive benefits of force F will be recognized regularly. Also, the magnitude of force F is greatest within the initial flexion range, specifically 0-30° of ulnar flexion. For example, at 26° of ulnar flexion, force F may reach a maximum average magnitude of approximately 1490 N. These high magnitude forces F will stabilize the connection between humeral yoke 32 and humeral stem 34.

On the other hand, during full flexion of ulnar component 20, the angle between force F and longitudinal axis 40 is greater than angle δ. For example, at 120° of ulnar flexion or more, the Average Joint Reaction Force Angle is greater than angle δ of 35° (See Table 1). Within that range, force F works against dovetail connection 80 between humeral yoke 32 and humeral stem 34. However, locking system 50 ensures that humeral yoke 32 remains locked onto humeral stem 34. It is important to note that the magnitude of force F is lowest within the full flexion range, specifically 90-145° of ulnar flexion, so locking system 50 only needs to be able to withstand these low magnitude forces F.

Although illustrated above with locking ball 70, locking system 50 may incorporate any other locking mechanism to provide an additional locking feature beyond dovetail connection 80 between humeral yoke 32 and humeral stem 34.

Figure 10:
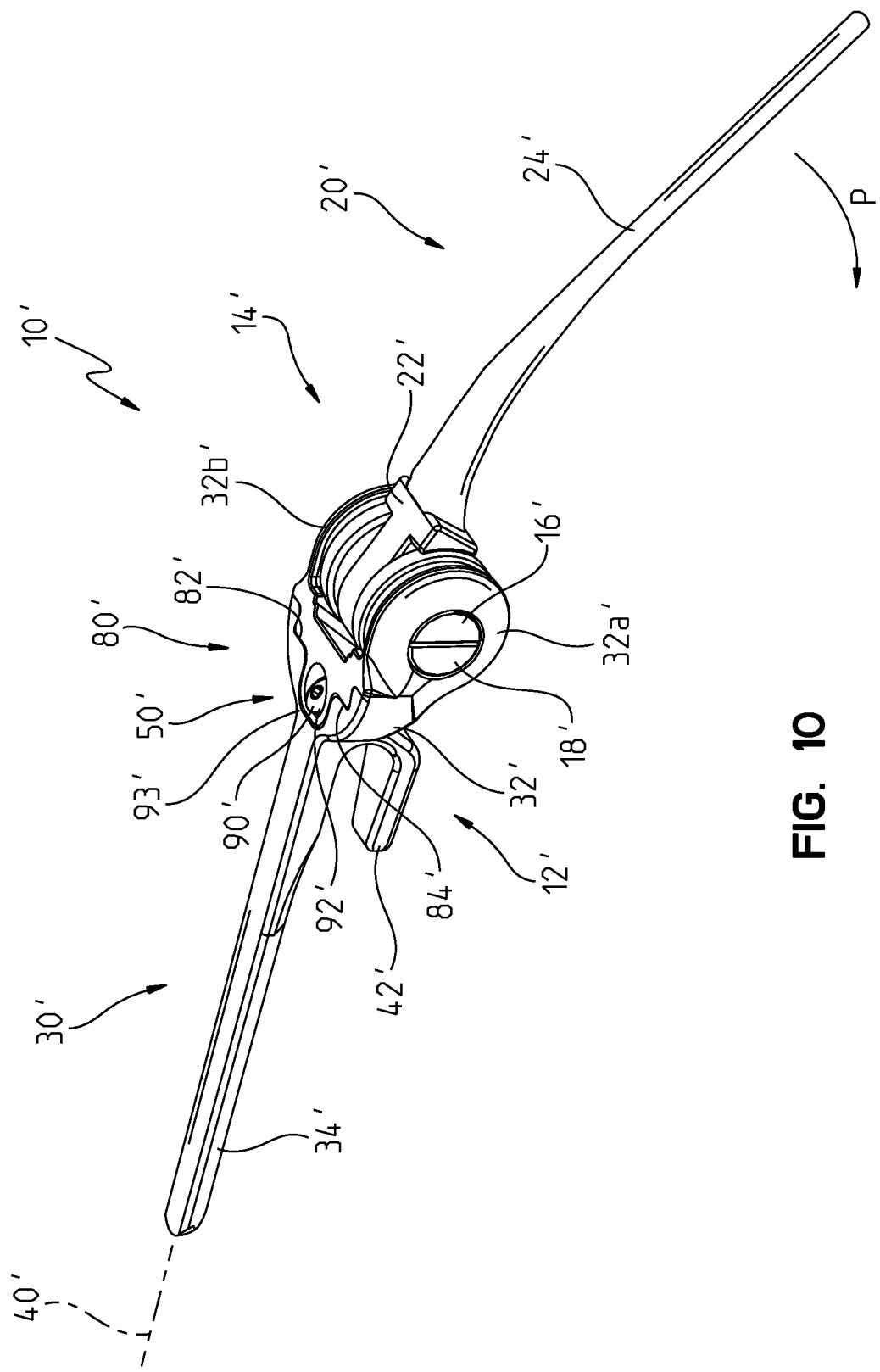
FIG. 10 is a perspective view of another exemplary elbow prosthesis of the present invention, the elbow prosthesis including an ulnar component and a humeral component.
Figure 11:
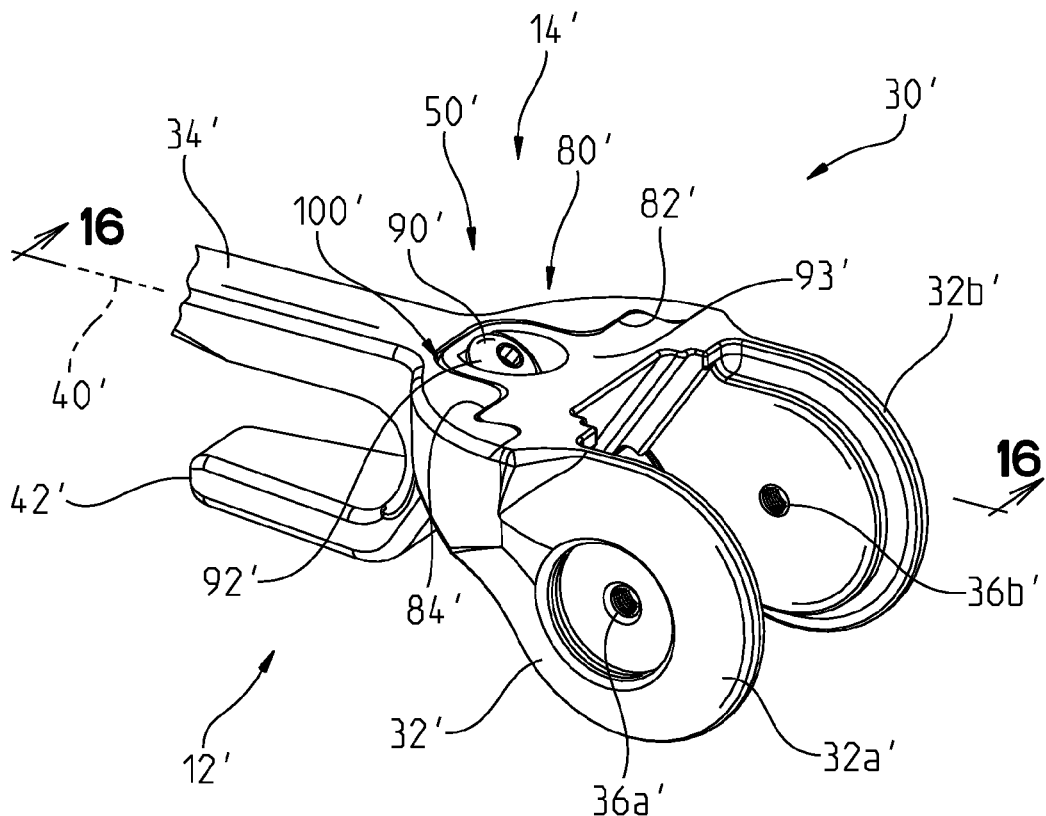
FIG. 11 is a perspective view of a portion of the humeral component of FIG. 10.
Figure 12:
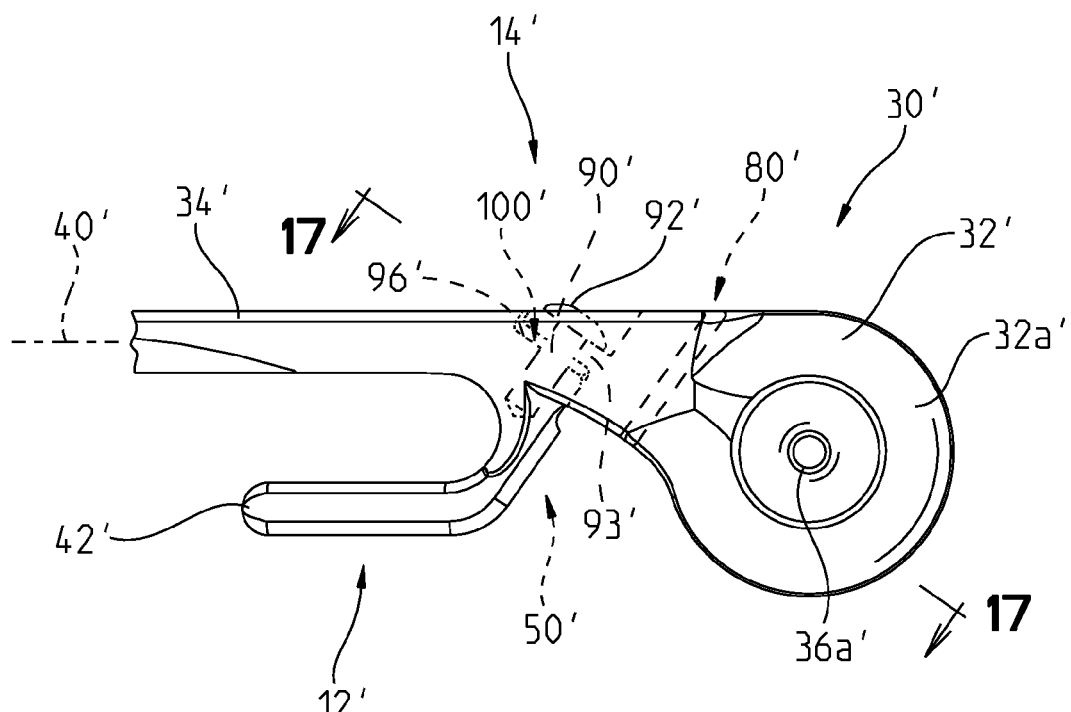
FIG. 12 is an elevational view of the humeral component of FIG. 11.

Another exemplary elbow prosthesis 10' is illustrated in FIG. 10. Elbow prosthesis 10' is substantially similar to elbow prosthesis 10 of FIG. 1, with like reference numerals indicating like elements, except as described below.

Figure 13:
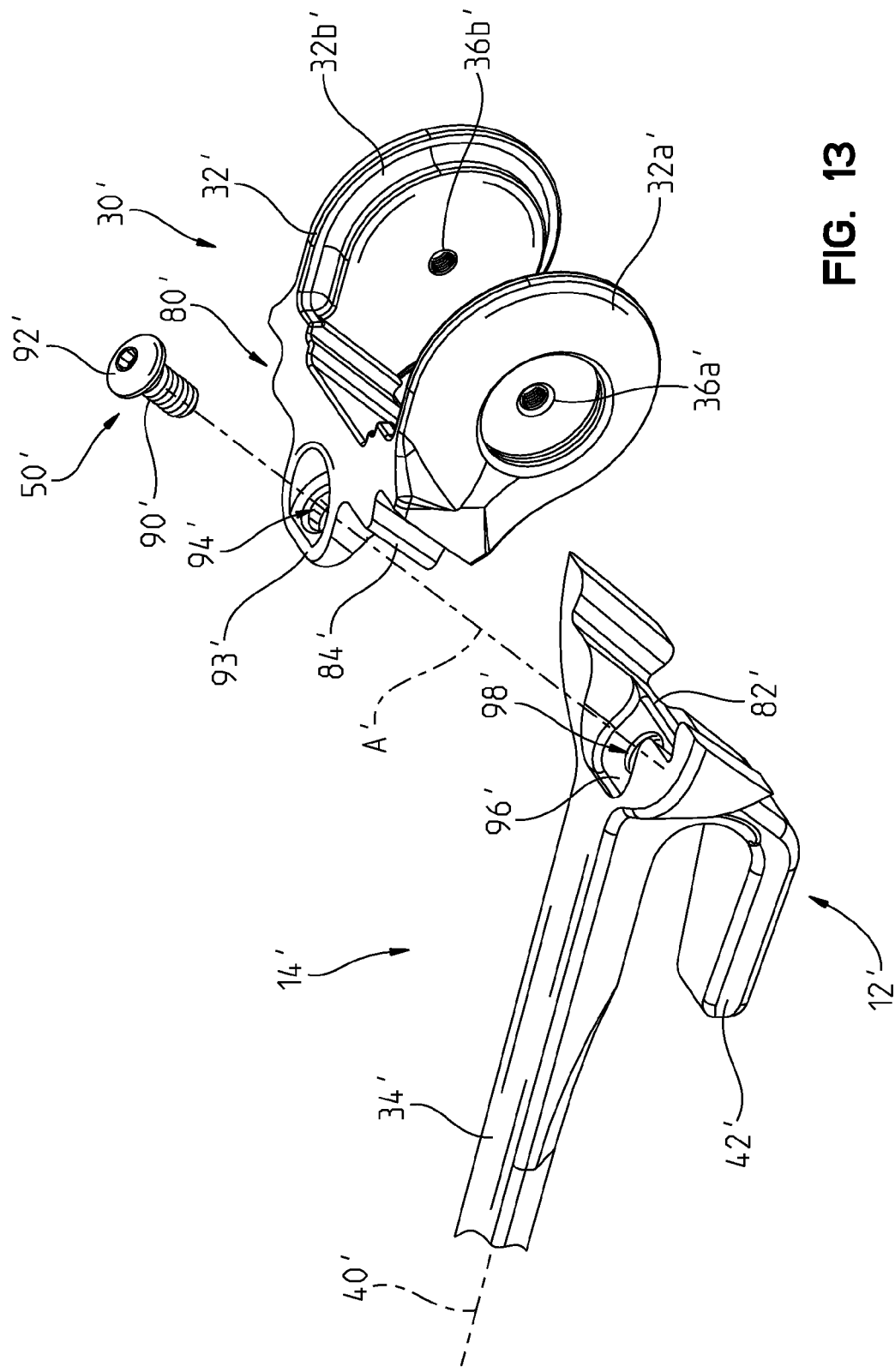
FIG. 13 is a posterior exploded perspective view of the humeral component of FIG. 11.

Referring to FIGS. 11-17, humeral component 30' includes locking system 50' for securing the desired humeral yoke 32' onto humeral stem 34'. Locking system 50' enables mating surface 52' of humeral yoke 32' to lock against mating surface 54' of humeral stem 34'. Locking system 50' includes an externally threaded screw 90' having head 92'. As shown in FIG. 13, humeral yoke 32' includes protrusion 93' having an internally threaded aperture 94', and humeral stem 34' includes a corresponding recess 96' having an internally threaded aperture 98'. In operation, the surgeon inserts protrusion 93' of humeral yoke 32' into recess 96' of humeral stem 34' to align apertures 94', 98'. Then, from posterior side 14, the surgeon screws screw 90' into apertures 94', 98', with head 92' resting atop protrusion 93' to lock humeral yoke 32' onto humeral stem 34'.

According to an exemplary embodiment of the present invention, humeral yoke 32' is connected to humeral stem 34' via a sliding connection, such as dovetail connection 80'. As shown by comparing FIG. 5 and FIG. 17, dovetail connection 80' is arranged opposite dovetail connection 80. Unlike humeral yoke 32 which includes a trapezoidal slot 82, humeral yoke 32' includes a trapezoidal rail 84'. Unlike humeral stem 34 which includes a trapezoidal rail 84, humeral stem 34' includes a trapezoidal slot 82'. Slot 82' of humeral stem 34' is sized to receive rail 84' of humeral yoke 32'. Mating surface 52' of humeral yoke 32' is located on the top of rail 84', and mating surface 54' of humeral stem 34' is located on the bottom of slot 82'. Like tab 88 of humeral stem 34 (FIG. 6), recess 96' of humeral stem 34' prevents excessive anterior movement of humeral yoke 32'.

Figure 14:
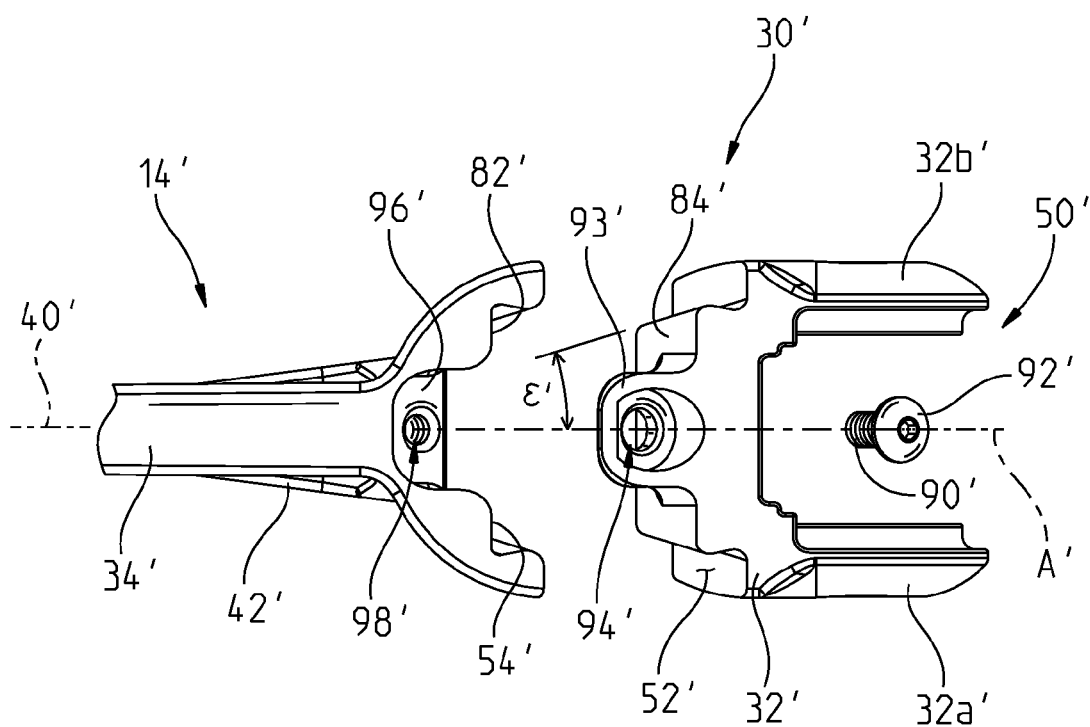
FIG. 14 is a posterior plan view of the humeral component of FIG. 11.
Figure 15:
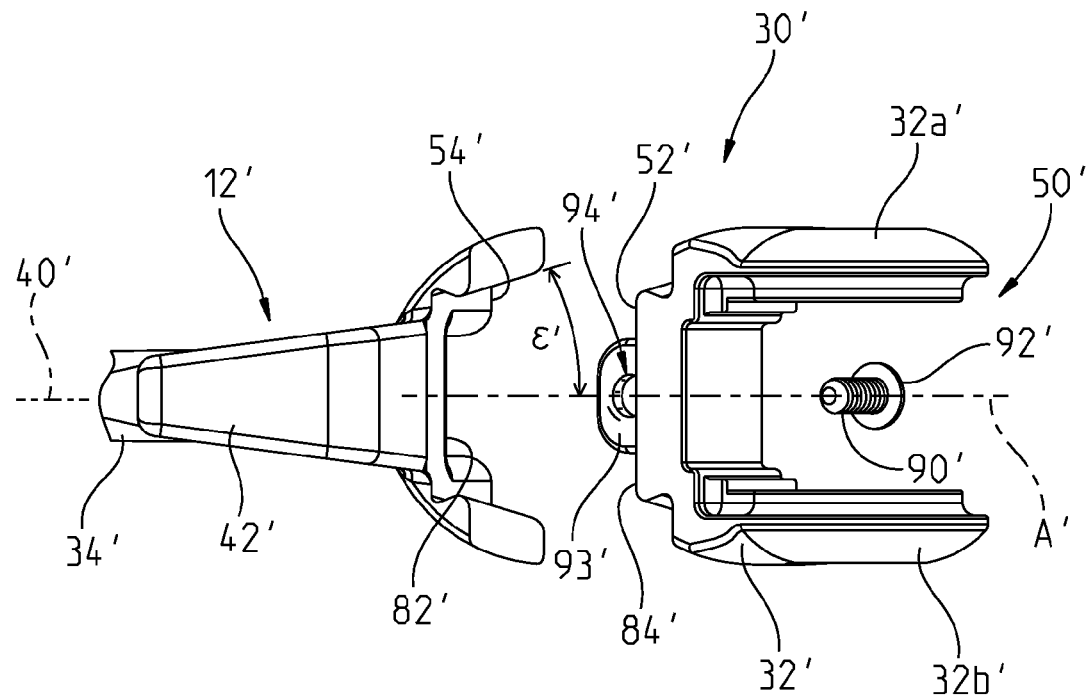
FIG. 15 is an anterior plan view of the humeral component of FIG. 11.

To stabilize the connection between humeral yoke 32' and humeral stem 34' and to reduce micro-motion, dovetail connection 80' may be a tapered connection. For example, as shown in FIGS. 14 and 15, slot 82' and rail 84' taper inwardly toward axis A' from posterior side 14' to anterior side 12' of humeral component 30'. More specifically, each side of slot 82' and rail 84' defines angle ε' with respect to axis A'. According to an exemplary embodiment of the present invention, angle ε' is approximately 5°, 10°, 15°, or more.

Figure 16:
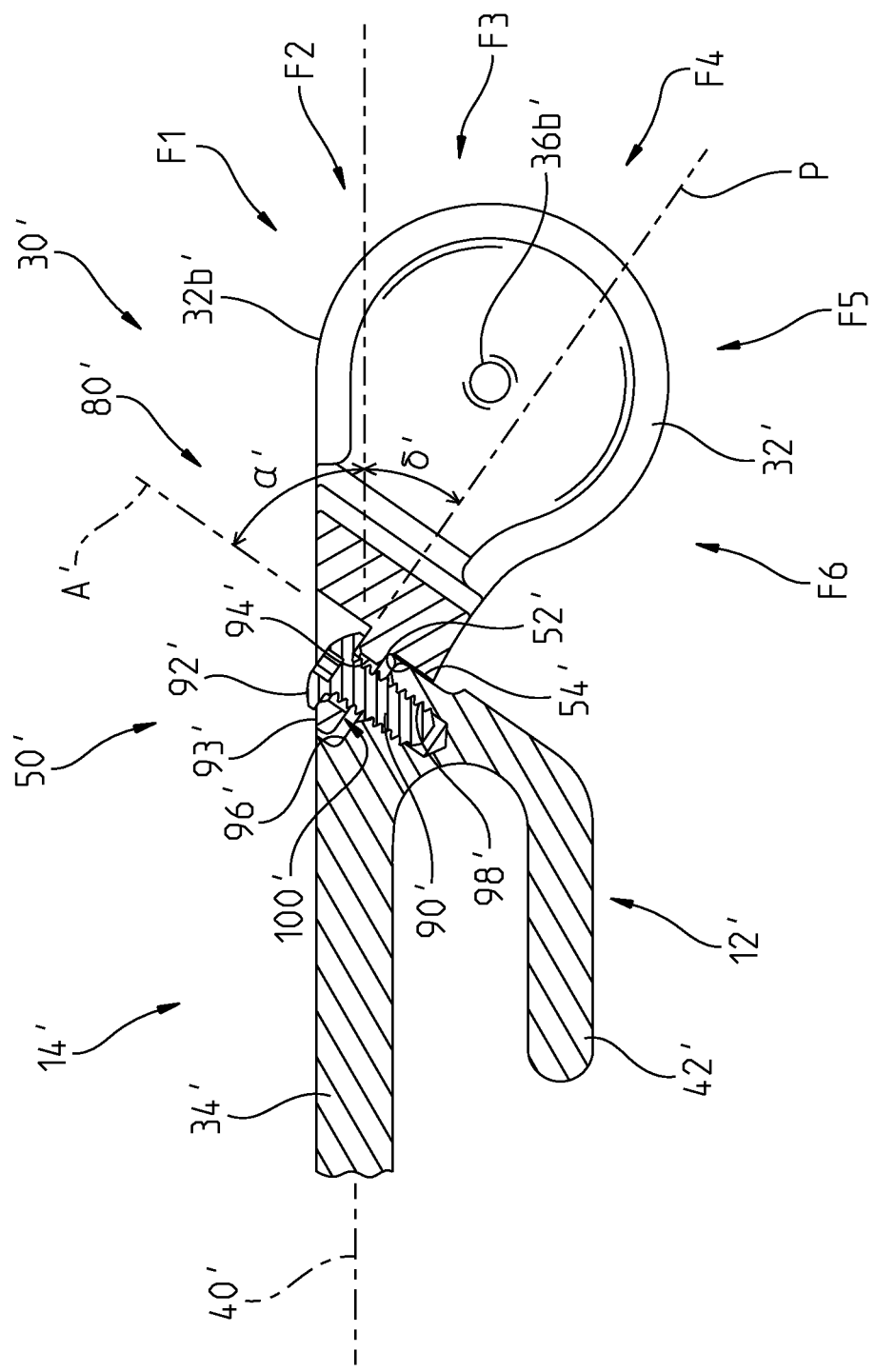
FIG. 16 is a cross-sectional view of the humeral component of FIG. 11, taken along line 16-16 of FIG. 11.
Figure 17:
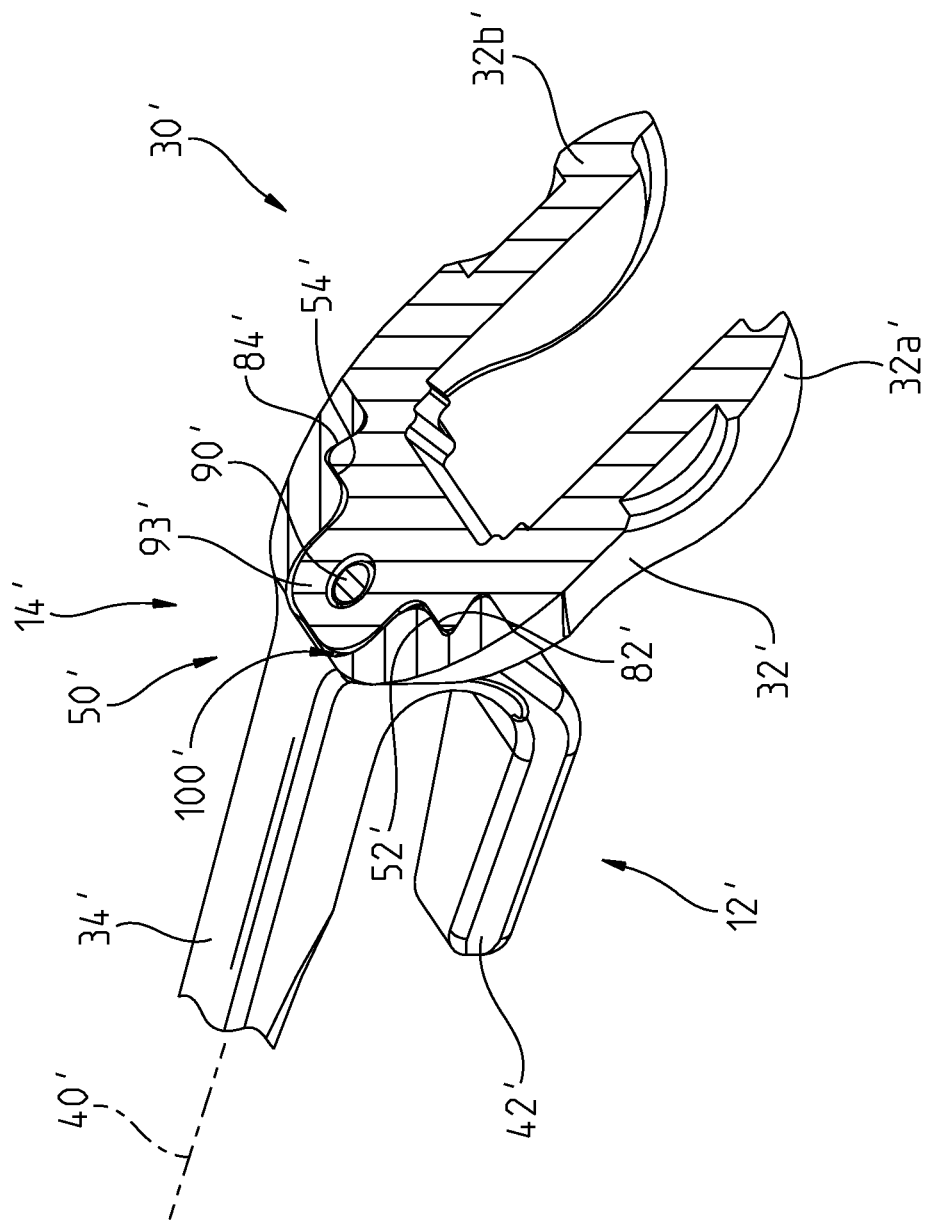
FIG. 17 is a cross-sectional view of the humeral component of FIG. 12, taken along line 17-17 of FIG. 12.

As shown in FIGS. 16 and 17, humeral yoke 32' is spaced apart from humeral stem 34' to define gap 100' therebetween. More specifically, protrusion 93' of humeral yoke 32' is substantially or entirely spaced apart from recess 96' of humeral stem 34' to define gap 100' therebetween. When humeral yoke 32' is being slid onto humeral stem 34', the surgeon is able to ensure that humeral yoke 32' is fully locked onto humeral stem 34' via dovetail connection 80', even before threading screw 90' in place, because gap 100' prevents premature contact between protrusion 93' of humeral yoke 32' and recess 96' of humeral stem 34' that would limit full locking of dovetail connection 80'.

While this invention has been described as having exemplary designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An elbow prosthesis having an anterior side and a posterior side, the elbow prosthesis comprising:
    a stem having a longitudinal axis, the stem comprising a first mating surface that extends from the posterior side of the elbow prosthesis toward the anterior side of the elbow prosthesis at a first angle relative to the longitudinal axis, wherein the stem is configured to be implanted into a bone, the stem including a channel extending from a first opening in the anterior side to a second opening in the first mating surface, the channel defining a second angle relative to the longitudinal axis, and wherein the stem includes a stop that faces the) posterior side of the elbow prosthesis;
    a head selectively coupled to the stem, the head comprising a second mating surface that abuts the first mating surface of the stem, the head comprising a first branch and a second branch that are spaced apart to define a space, wherein the space is configured to receive an ulnar head of an ulnar component, and wherein the stop contacts the head to prevent removal of the head from the anterior side of the elbow prosthesis; and
    a lock that releasably secures the head onto the stem.

2. The elbow prosthesis of claim 1, wherein the lock includes a spring and a ball that is sized for receipt within a recess in one of the stem and the head.

3. The elbow prosthesis of claim 2, wherein the channel holds the spring and the ball, and the head includes the recess, wherein the ball protrudes toward the recess in the head through the second opening.

4. The elbow prosthesis of claim 1, wherein the lock includes a screw, the head defining an aperture, the aperture and the second opening cooperate to receive the screw.

5. The elbow prosthesis of claim 1, wherein the first mating surface angles proximally from the posterior side to the anterior side of the elbow prosthesis.

6. The elbow prosthesis of claim 1, wherein the first angle is within a range of from approximately 45 degrees and 65 degrees.

7. The elbow prosthesis of claim 6, wherein the first angle is 55 degrees.

8. The elbow prosthesis of claim 1, wherein one of the stem and the head includes a trapezoidal rail and the other of the stem and the head includes a corresponding trapezoidal slot that is sized to receive the trapezoidal rail.

9. The elbow prosthesis of claim 8, wherein the trapezoidal rail and t trapezoidal slot taper inwardly from the posterior side of the elbow prosthesis toward the anterior side of the elbow prosthesis.

10. The elbow prosthesis of claim 1, wherein the stem includes a flange that extends from the anterior side of the elbow prosthesis to stabilize the stem in a bone.

11. An elbow prosthesis comprising:
    a stem having a longitudinal axis and configured to be implanted into a bone, the stem comprising a first mating surface extending from a posterior side of the elbow prosthesis toward an anterior side of the elbow prosthesis at a first angle relative to the longitudinal axis, wherein the stem includes a channel extending from a first opening in the anterior side to a second opening in the first mating surface, and the channel defines a second angle relative to the longitudinal axis;
    a head comprising a first branch and a second branch that are spaced apart to define a space, wherein the space is configured to receive an ulnar head of an ulnar component;
    a sliding connection including a rail that extends from one of the stem and the head and a slot formed in the other one of the stem and the head, the rail being sized to slide within the slot along a sliding axis to couple the head to the stem, the sliding axis and the longitudinal axis defining a third angle therebetween, wherein the sliding connection enables removal of the head from the posterior side of the stem; and
    a locking feature for releasably securing the head onto the stem.

12. The elbow prosthesis of claim 11, wherein the stem includes a stop that faces the posterior side of the elbow prosthesis, the stop contacting the head to prevent removal of the head from the anterior side of the stem.

13. The elbow prosthesis of claim 11, wherein the sliding axis extends proximally from the posterior side to the anterior side of the elbow prosthesis.

14. The elbow prosthesis of claim 11, wherein the first angle is within a range of from approximately 45 degrees to 65 degrees.

15. The elbow prosthesis of claim 14, wherein the first angle is 55 degrees.

16. The elbow prosthesis of claim 11, wherein the rail and the slot are trapezoidal in shape.

17. A method for repairing a bone of a patient's elbow joint, the method comprising the steps of:
   providing an elbow prosthesis including a head and a stem, the elbow prosthesis having an anterior side and a posterior side, the stem having a longitudinal axis, the stem comprising a first mating surface that extends from the posterior side of the elbow prosthesis toward the anterior side of the elbow prosthesis at a first angle relative to the longitudinal axis, wherein the stem includes a channel extending from a first opening in the anterior side to a second opening in the first mating surface and the channel defines a second angle relative to the longitudinal axis, wherein the stem includes a stop that faces the posterior side of the elbow prosthesis, the head comprises a second mating surface configured to abut the first mating surface of the stem, and the head includes a first branch and a second branch that are spaced apart to define a space, wherein the space is configured to receive an ulnar head of an ulnar component;
   sliding the head from the posterior side of the elbow prosthesis toward the anterior side of the elbow prosthesis along a sliding axis that is angled relative to the longitudinal axis to couple the head to the stem;
   releasably locking the head onto the stem; and
   implanting the stem into the bone.

18. The method of claim 17, wherein the locking step comprises forcing a locking ball into a recess of the head.

19. The method of claim 17, wherein the locking step comprises screwing the head onto the stem.

20. The method of claim 17, wherein the sliding axis is acute relative to the longitudinal axis of the stem.

21. The method of claim 17, wherein the sliding axis extends proximally from the posterior side to the anterior side of the elbow prosthesis.

22. The method of claim 17, wherein the implanting step precedes the sliding and locking steps.

* * * * *

UNITED STATES PATENT AND TRADEMARK OFFICE
CERTIFICATE OF CORRECTION

PATENT NO. : 8,968,411 B2
APPLICATION NO. : 12/856112
DATED : March 3, 2015
INVENTOR(S) : Wagner et al.

Page 1 of 1

It is certified that error appears in the above-identified patent and that said Letters Patent is hereby corrected as shown below:

On the Title page, in item (75), in "Inventors", in column 1, line 1, delete "Michawaka," and insert --Mishawaka,--, therefor In the Claims In column 7, line 61, in Claim 1, delete "the)" and insert --the--, therefor In column 8, line 28, in Claim 9, before "trapezoidal", delete "t", therefor Signed and Sealed this
Twenty-fifth Day of August, 2015

Michelle K. Lee
*Director of the United States Patent and Trademark Office*